United States Patent
Kahlman et al.

(10) Patent No.: US 9,339,813 B2
(45) Date of Patent: May 17, 2016

(54) SUBSTANCE DETERMINING APPARATUS

(75) Inventors: Josephus Arnoldus Henricus Maria Kahlman, Tilburg (NL); Joannes Baptist Adrianus Dionisius Van Zon, Waalre (NL); Johannes Joseph Hubertina Barbara Schleipen, Eindhoven (NL); Derk Jan Wilfred Klunder, Geldrop (NL); Toon Hendrik Evers, Eindhoven (NL); Ron Martinus Laurentius Van Lieshout, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 37 days.

(21) Appl. No.: 13/516,060

(22) PCT Filed: Dec. 10, 2010

(86) PCT No.: PCT/IB2010/055723
§ 371 (c)(1),
(2), (4) Date: Aug. 31, 2012

(87) PCT Pub. No.: WO2011/073867
PCT Pub. Date: Jun. 23, 2011

(65) Prior Publication Data
US 2012/0329039 A1    Dec. 27, 2012

(30) Foreign Application Priority Data

Dec. 18, 2009  (EP) .................................... 09179976

(51) Int. Cl.
*G01N 21/17*  (2006.01)
*B01L 3/00*  (2006.01)
(Continued)

(52) U.S. Cl.
CPC ............ *B01L 3/5027* (2013.01); *G01N 21/552* (2013.01); *G01N 21/8483* (2013.01);
(Continued)

(58) Field of Classification Search
None
See application file for complete search history.

(56) References Cited

U.S. PATENT DOCUMENTS 7,255,995 B2    8/2007    Yguerabide
2001/0002315 A1*  5/2001  Schultz et al. ................ 436/172
(Continued)

FOREIGN PATENT DOCUMENTS

CN    1223692 A    7/1997
WO    9958948 A2    11/1999
(Continued)

OTHER PUBLICATIONS

Pamme et al., Magnetism and Microfluidics, Lab on a Chip, 6, pp. 24-28, available online Nov. 28, 2005.*
(Continued)

*Primary Examiner* — Melanie Y Brown
*Assistant Examiner* — Rebecca Martinez

(57) ABSTRACT

The invention relates to a substance determining apparatus for determining a substance within a fluid. Particles attach the substance and bind to a binding surface (30), wherein a sensing signal is generated depending on the bound particles. Binding events indicating a binding of a particle on the binding surface (30) are determined from the generated sensing signal, and the substance within the fluid is determined based on the determined binding events. During a procedure of determining a substance within a fluid, particles may bind to the binding surface and may leave the binding surface. Therefore, during this procedure a number of binding events can be determined being much larger than the number of bound particles. The determination of the substance within the fluid can therefore be based on a very large amount of data, thereby increasing the accuracy of determining the substance within the fluid.

12 Claims, 6 Drawing Sheets

(51) Int. Cl.
*G01N 21/552* (2014.01)
*G01N 21/84* (2006.01)
*G01N 33/543* (2006.01)

(52) U.S. Cl.
CPC ... *G01N33/54373* (2013.01); *B01L 2200/0605* (2013.01); *B01L 2300/0636* (2013.01); *B01L 2300/0681* (2013.01); *B01L 2300/0816* (2013.01); *B01L 2400/0406* (2013.01)

(56) References Cited

U.S. PATENT DOCUMENTS

| | | | |
|---|---|---|---|
| 2006/0019267 A1* | 1/2006 | Quake | 435/6 |
| 2008/0241858 A1 | 10/2008 | Metzger | |
| 2009/0004757 A1 | 1/2009 | Yguerabide | |
| 2009/0062130 A1 | 3/2009 | Steinman | |
| 2009/0095911 A1* | 4/2009 | Kim et al. | 250/363.01 |

FOREIGN PATENT DOCUMENTS

| | | |
|---|---|---|
| WO | 2009083814 A2 | 7/2009 |
| WO | 2009093160 A1 | 7/2009 |
| WO | 2009098623 A1 | 8/2009 |
| WO | 2009125356 A1 | 10/2009 |

OTHER PUBLICATIONS

Hiddessen et al., Influence of Biomolecular Site Density on Particle Interaction Lifetimes in Receptor-mediated Colloidal Assembly, Department of Bioengineering Univ. of Pennsylvania, pp. 1-44.*

Schulte, Roberta et al "Single Bead Affinity Detection (SINBAD) for the Analysis of Protein-Protein Interactions" Molecular and Cell Biology Laboratory, Salk Institute for Biologicla Studies, La Jolla, CA, 2008, pp. 1-11.

Yu Feng Shang et al, "Dynamic light scattering experiment", Physics Experimentation, vol. 24, No. 10, (2004), pp. 9-11.

Juan Yguerabide, Light-Scattering Submicroscopic Particles as Highly Fluorescent Analogs and Their Use as tracer Labels in Clinical and Biological Applications, Analytical Biochemistry, vol. 262, No. 2, (1998), pp. 137-156.

* cited by examiner

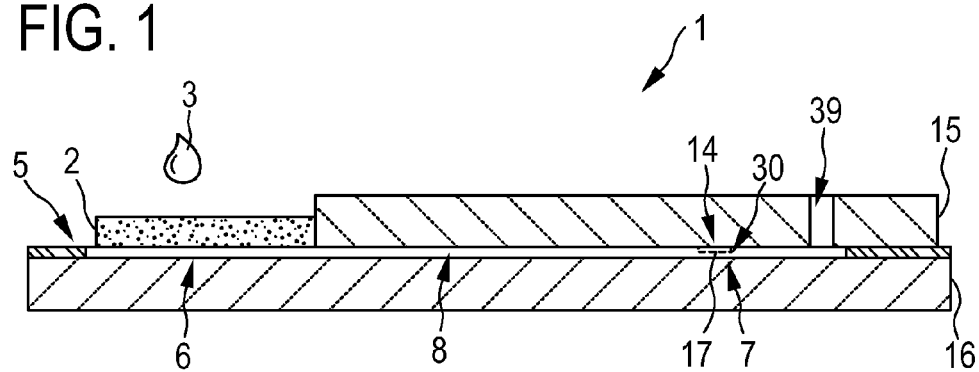
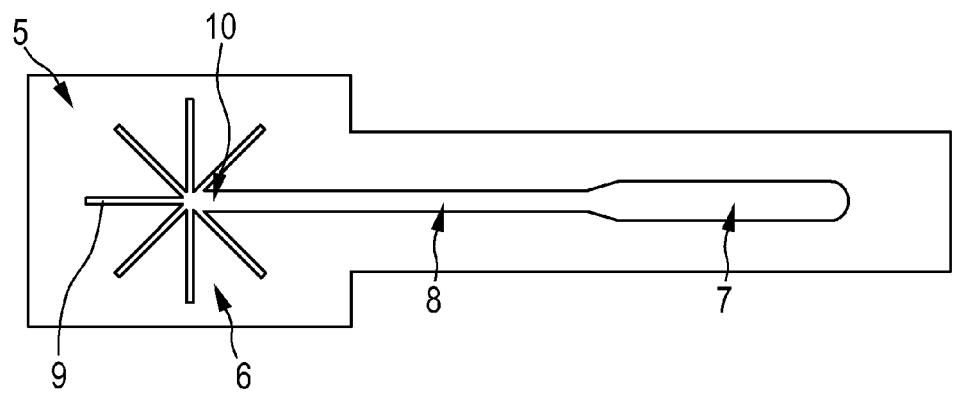
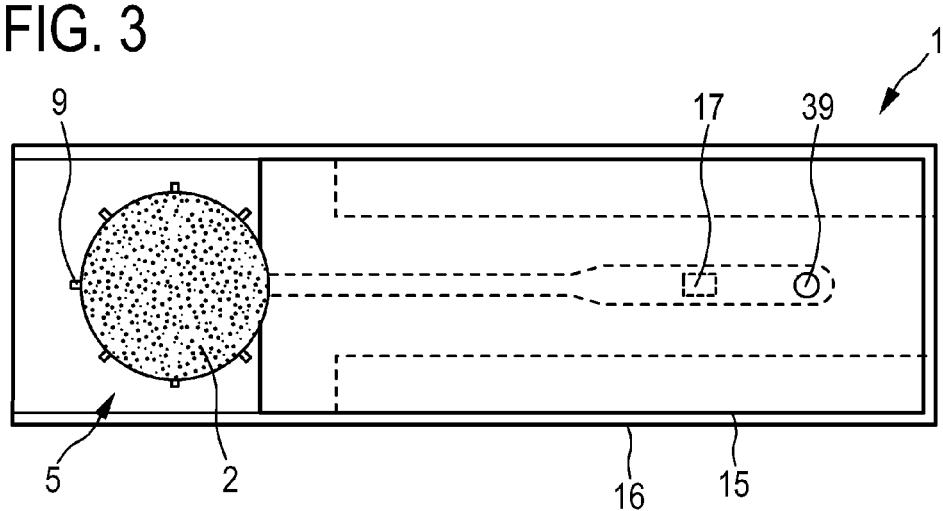

SUBSTANCE DETERMINING APPARATUS

FIELD OF THE INVENTION

The invention relates to a substance determining apparatus and substance determining method for determining a substance within a fluid. The invention relates further to a binding device and an analyzing device for cooperating with each other for determining a substance within a fluid, to an analyzing method for determining a substance within a fluid, and an analyzing computer program for determining a substance within a fluid.

BACKGROUND OF THE INVENTION

WO 2009/098623 A1 discloses a magnetic biosensor based on magnetic beads that can be actuated with electromagnetic fields. The magnetic beads are functionalized with antibodies that can bind a specific analyte molecule in a sample. The beads are attracted to the sensor surface, where the number of bound beads is directly or inversely related to the amount of analyte molecules present in the sample. The beads are then detected by a technique which is based on frustrated total internal reflection (FTIR).

SUMMARY OF THE INVENTION

It is an object of the present invention to provide a substance determining apparatus and substance determining method for determining a substance within a fluid, which allows increasing the accuracy of determining the substance. It is a further object of the present invention to provide a corresponding binding device and analyzing device for cooperating with each other for determining a substance within a fluid, an analyzing method for determining a substance within a fluid, and an analyzing computer program for determining a substance within a fluid.

In a first aspect of the present invention a substance determining apparatus for determining a substance within a fluid is presented, wherein the substance determining apparatus comprises:
  particles for being attached to the substance within the fluid,
  a binding surface for binding the particles, if the particles have been attached to the substance,
  a sensing unit for sensing the particles on the binding surface, wherein the sensing unit is adapted to generate a sensing signal depending on the bound particles,
  a binding event determination unit for determining binding events indicating a binding of a particle on the binding surface from the generated sensing signal,
  a substance determination unit for determining the substance within the fluid based on the determined binding events.

In the prior art bound particles are sensed and a substance within the fluid, in particular, the amount, the concentration or a property, in particular, a molecular property, like a binding reaction constant of the substance within the fluid, is determined based on the bound particles. However, during a procedure of determining a substance within a fluid, particles may bind to the binding surface and may leave the binding surface. Therefore, during this procedure a number of binding events can be determined being much larger than the number of bound particles. The determination of the substance within the fluid can therefore be based on a very large amount of data, thereby allowing the substance determination unit to increase the accuracy of determining the substance within the fluid.

The substance determining apparatus is preferentially a magnetic biosensor, wherein the particles are magnetic beads, i.e. nanoparticles, which label the substance. The magnetic beads are preferentially functionalized with an attaching element that can be attached to the substance being, for example, a specific analyte molecule. The attaching element is, for example, an antibody, a protein, DNA, an aptamer et cetera. The substance determination apparatus is preferentially adapted to perform a sandwich immunoassay.

The substance determining apparatus preferentially comprises a magnetic unit for attracting the magnetic beads to the binding surface and/or for pulling the magnetic beads away from the binding surface.

The sensing unit can be any unit which uses a technique that allows generating a sensing signal being dependent on the bound particles.

A binding event can be characterized by, for example, a transition of a particle going from an unbound state to a bound state (U=>B), a transition of a particle going from a bound state to an unbound state (B=>U) or as the lifetime of a binding event defined as the time which has passed between the (U=>B) transition and (B=>U) transition. The binding event determination unit can therefore be adapted to determine, for example, the number of (U=>B) transitions per unit time at a certain time for determining a particle arrival rate or to determine the number of (B=>U) transitions per unit time at a certain time as a particle desorption rate. Moreover, the binding event determination unit can be adapted to determine lifetimes of binding events as the time which has passed between a starting moment being a (U=>B) transition and an ending moment being a (B=>U) transition. If a particle is still bound at the end of the measurement of the sensing signal, in particular, at the end of a washing phase, an ending moment can be defined as a moment at which the measurement of the sensing signal is stopped. Preferentially, the sensing unit is adapted such that the generated sensing signal is indicative of starting moments and ending moments of binding events, in particular, of single binding events, wherein the binding event determination unit is adapted to determine the lifetimes of binding events by determining the starting moments and the ending moments of the single binding events from the generated sensing signal. In particular, the sensing unit is adapted to generate images of the binding surface at different times as the sensing signal, wherein an image shows at which positions on the binding surface particles are bound at a time, wherein the binding event determination unit is adapted to determine the starting moments and the ending moments by comparing temporally consecutive images. This allows determining binding events and lifetimes of the binding events with low computational efforts by simply comparing temporally consecutive images. The positions are preferentially in-plane positions of the particles bound on the binding surface, i.e. positions of the particles within a plane defined by the binding surface or being parallel to the binding surface.

The substance determination unit is preferentially adapted to determine the amount or the concentration of the particles within the fluid.

The sensing unit preferentially comprises a light source for generating radiation for being directed to the binding surface for generating an evanescent field and a light detector for detecting light from the binding surface, wherein the detected light has been influenced by the particles bound on the binding surface by influencing the evanescent field, and wherein the images are generated from the detected influenced light.

Preferentially, evanescent light is scattered by the particles bound on the binding surface, and the scattered light is detected by the light detector.

The light source preferentially comprises a light emitting diode or a laser for exciting the evanescent field.

The sensing unit preferentially comprises an objective lens for collecting the light of the evanescent field scattered by the bound particles on the binding surface, wherein the collected scattered light is imaged onto a two-dimensional light detector like a CCD- or CMOS-camera by an imaging unit like an imaging lens. This allows using dark field microscopy (DFM) for generating a sensing signal.

It is further preferred that the substance determination unit is adapted to generate a histogram of lifetimes of the binding events and to determine the substance within the fluid based on the histogram. Preferentially, the substance determination unit is adapted to
- determine a part of the histogram depending on a temporal behaviour of the histogram being indicative of a certain kind of binding,
- determine the substance within the fluid based on the determined part of the histogram being indicative of the certain kind of binding. The temporal behaviour of a histogram can, for example, be defined by a superposition of exponential decay curves having different time constants. This superposition of exponential decay curves can be fitted to the histogram, wherein the time constant and the amplitude of the respective exponential decay function can be fitting parameters. Preferentially, the substance determination unit comprises assignments between one or several time constants and the certain kind of binding. An exponential decay curve with a time constant assigned to the certain kind of binding or a combination of exponential decay curves with time constants assigned to a certain kind of binding is preferentially determined as the part of the histogram being indicative of the certain kind of binding. The certain kind of binding is, for example, a specific binding of a particle.

In an embodiment, the substance determination unit is adapted to
- provide a fitting curve comprising a combination of a) a first product of a first number of binding events with a predefined lifetime and a first exponential decay fitting curve having a first time constant and b) a second product of a second number of binding events with the predefined lifetime and a second exponential decay fitting curve having a second time constant,
- fit the fitting curve to the histogram, wherein the first number of binding events, the first time constant, the second number of binding events and the second time constant are fitting parameters,
- determine the part of the histogram being indicative of the certain kind of binding substance depending on at least one of the first exponential decay fitting curve with the fitted first number of binding events and first time constant and the second exponential decay fitting curve with the fitted second number of binding events and second time constant. Thus, the fitting curve is preferentially a linear combination of several exponential decay curves, which is fitted to the histogram. A substance, in particular, a concentration or amount of the substance, within the fluid is then preferentially determined based on one or several of the fitted exponential decay curves. Different kinds of binding between particles and binding surface can lead to different time constants which are defined by different reaction constants $k_{off}$. Thus, by determining the substance, i.e. e.g. the amount and/or concentration of the substance within the fluid depending on one or several of the exponential decay fitting curves the substance can be determined depending on the kind of binding, for example, depending on the strength of the binding. For instance, for determining the substance only binding events can be considered, which correspond to one or several certain kinds of binding. This allows, for example, distinguishing between different kinds of particles in the fluid, if they are bound to the binding surface with different kinds of binding. Moreover, this allows to distinguish between specific and non-specific binding, wherein the substance determination unit can be adapted to use only specific binding events for determining the substance. This further improves the accuracy of determining a substance within a fluid.

In particular, when measuring low analyte concentrations, the sensitivity is generally determined by the signal that is obtained for a low concentration and the signal that is obtained for a blank measurement, containing no analyte. It is observed that the signal for the blank measurement is not only determined by instrument noise, but that an additional signal can be generated by particles binding to the surface, independent of the presence of an analyte, i.e. that an additional signal is generated by non-specific binding. Since this non-specific binding can occur, increasing the instrumental signal per particles may not increase the overall sensitivity, as the signal for the non-specific binding may also be increased. But, since the substance determination unit can be adapted to consider only specific binding events, as already mentioned above, the accuracy of determining the substance within the fluid can be further improved.

Specifically bound particles are preferentially particles which have been attached to the substance and which have been bound to the binding surface. In particular, a specific binding is preferentially a binding that depends on the presence of the substance, i.e. it preferentially describes a binding, wherein a particle has been attached to the substance and is bound to the binding surface, whereas non-specific binding is preferentially a binding that is not dependent on the presence of the substance, i.e. it preferentially describes a presence of particles on the binding surface, wherein the particles have not been attached to the substance. The substance determination unit can be adapted to determine the amount of specifically bound particles on the binding surface.

It is further preferred that the substance determination unit is adapted to modify the histogram by differentiating the histogram with respect to the lifetime and multiplying the differentiated histogram with the lifetime, to determine extremal lifetimes at which the modified histogram has an extremum and to determine the substance depending on the determined extremal lifetimes. In particular, the substance determination unit is adapted to determine time constants as the inverse of the determined extremal lifetimes, to provide a fitting curve comprising combinations of products of numbers of binding events with a predefined lifetime and exponential decay fitting curves having the determined time constants, to fit the fitting curve to the histogram, wherein the numbers of binding events with the predefined lifetime are fitting parameters, and to determine the part of the histogram being indicative of the certain kind of binding depending on at least one of the products of fitted numbers of binding events with a predefined lifetime and the exponential decay fitting curve with the determined time constant. The fitting curve is preferentially fitted to the unmodified histogram.

The extremal lifetimes and the corresponding time constants are indicative of the respective kind of binding. Thus, it can be distinguished between different kinds of binding, wherein the different extremal lifetimes and the corresponding time constants can be used for distinguishing between, for example, different kinds of particles and/or specifically and non-specifically bound particles. This allows the substance determination unit to determine the amount and/or concentration of certain kinds of particles and/or of specifically bound particles depending on one or several determined extremal lifetimes or the corresponding one or several time constants.

As already mentioned above, the time constant and, thus, the corresponding extremal lifetime are defined by the reaction constant $k_{off}$ of the respective kind of binding. The reaction constant $k_{off}$ specifies the release rate of the respective binding in release events per second. For example, a strong binding will have a low release rate of, for instance, $10^{-5}$ s$^{-1}$, while a weak binding will have a high release rate of, for instance, $10^{-2}$ s$^{-1}$. This difference in the release rates and, thus, in the reaction constant $k_{off}$ can be used to discriminate between specific and non-specific bindings.

It is further preferred that the sensing unit comprises a force applying unit for applying a force to the particles for putting bindings between the particles and the binding surface under stress, while sensing the particles. By applying a force to the particles for putting bindings between the particles and the binding surface under stress, while sensing the particles, the starting moments and/or ending moments of the binding events can be modified. The force can be applied to the particles such that the differences between the different kinds of binding are more pronounced, for example, such that different time constants indicating different kinds of binding can more easily be determined, in particular, separated from each other. Preferred forces can be determined by calibration.

The force applying unit is preferentially a magnetic unit for applying magnetic forces to the particles bound to the binding surface. The particles are preferentially particles which can be forced by a magnetic field. The magnetic unit can be adapted such that the particles can be attracted towards the binding surface or pulled away from the binding surface. The magnetic unit can also be adapted to modify the in-plane position of the bound particles, i.e. to move the particles in a lateral direction parallel to the binding surface. Moreover, the magnetic unit can be adapted such that the orientation of the particles, which are preferentially magnetic particles, can be modified.

In addition to or in an alternative, the force applying unit can be adapted to apply another force to the particles for putting the bindings between the particles and the binding surface under stress. For example, the force applying unit can be adapted to apply fluidic, electrostatic, sonic, et cetera, forces to the particles bound to the binding surface. In particular, an ionic content of the fluid can be modified for modifying the distance of the particles bound to the binding surface and the binding surface, thereby modifying the stress applied to the bindings.

The substance determining apparatus is preferentially adapted to provide a binding phase and a washing phase. In the binding phase the force applying unit forces the particles towards the binding surface, in order to allow the particles to be bound to the binding surface, and preferentially the unbound particles away from the binding surface in an alternating way, i.e. in the binding phase preferentially the force applying unit forces the particles alternately towards the binding surface and away from the binding surface. In the binding phase particles can be bound to the binding surface and bindings can be broken. In the following washing phase the force applying unit applies a force to the particles, which urge the particles only away from the binding surface, thereby washing unbound particles away from the binding surface and putting the bindings between bound particles and the binding surface under stress. In the washing phase preferentially new bindings are not generated and also bound particles are released from the binding surface. The sensing unit can be adapted to sense the particles on the binding surface during the binding phase and/or during the washing phase, wherein the binding event determination unit can be adapted to determine lifetimes of binding events from the generated sensing signal in the binding phase and/or in the washing phase. In an embodiment, a histogram of the lifetimes of the binding events can be formed, which is relevant to the binding phase and/or in the washing phase and time constants and, thus, corresponding reaction constants can be determined by fitting exponential decay curves to the histogram. The substance determination unit then preferentially determines the substance within the fluid based on the fitting results, in particular, based on the fitted time constants and, thus, based on the fitted reaction constants. The substance determining apparatus can therefore be adapted to determine the substance within the fluid based on binding events and lifetimes in the binding phase and/or in the washing phase.

The substance determination unit can comprise assignments between time constants and a certain kind of binding and between amplitudes of parts of the histogram being indicative of the certain kind of binding and the amount and/or concentration of the corresponding substance within the fluid. The assignments between time constants and a certain kind of binding can be used to determine the part of the histogram being indicative of the certain kind of binding, and the assignment between the amplitude of the part of the histogram being indicative of the certain kind of binding and the amount and/or concentration of the corresponding substance within the fluid can be used to determine the amount and/or concentration of the respective substance to be determined. An assignment between a time constant and a certain kind of binding can be determined by calibration. For example, time constants of the histogram can be determined, if only a single known kind of binding is present. An assignment between the amplitude of the respective part of the histogram being indicative of the certain kind of binding and an amount and/or concentration of a corresponding substance within the fluid can also be determined by calibration, wherein the amplitude of the part of the histogram being indicative of the certain kind of binding is determined, if the amount and/or concentration of the corresponding substance within the fluid is known.

The substance determination unit can be adapted to determine a reaction constant $k_{on}$ from a particle arrival rate. The reaction constant $k_{on}$ is indicative of the probability of a certain kind of binding. In addition or alternatively, the substance determination unit can be adapted to determine the chemical reaction constant $k_{off}$ depending on a particle desorption rate. The particle desorption rate is proportional to the chemical reaction constant $k_{off}$ and the concentration of particles on the surface and can therefore be used to determine the chemical reaction constant $k_{off}$ from the particle desorption rate. The substance determination unit is preferentially adapted to determine, for example, the concentration or amount of a substance within the fluid based on the chemical reaction constants $k_{on}$ and/or $k_{off}$.

The binding event determination unit can be adapted to use single binding events to construct particle arrival rates, particle desorption rates and/or particle release curves separately under conditions where arrival and/or desorption of particles are both continuously present, for example, in the binding phase. However, the binding event determination can also be adapted to determine particle arrival rates only in a phase, in which only arriving particles are present, for example, if the particle bind very well and no desorption is present, and/or to determine particle desorption rates and/or particle release curves in the washing phase only. The obtained information can be used by the substance determination unit to determine a substance within the fluid, i.e. e.g., to determine a concentration of a substance or a chemical property of a substance like a bound strength, an affinity et cetera.

The substance determination apparatus preferentially comprises a binding device, in particular, a cartridge, including the particles and the binding surface and being adapted to receive the fluid, and an analyzing device, which can be regarded as a reader, including the sensing unit, the binding event determination unit and the substance determination unit.

The binding device is preferentially a disposable device and the analyzing device is preferentially a reusable device. Thus, by distributing the functionalities over the binding device and the analyzing device, a part of the substance determination apparatus can be used as a disposable device and the other part can be used as a reusable device. Since the fluid, which is preferentially a sample of a bodily fluid like blood, saliva or urine, is introduced into the binding device and since the binding device is a disposable device, the binding device can be used only one time before being disposed, i.e. a determination of the substance within the fluid is not affected by impurities of a previous measurement.

In an aspect of the present invention a binding device for cooperating with an analyzing device for determining a substance within a fluid is presented, wherein the binding device comprises
    particles for being attached to the substance within the fluid,
    a binding surface for binding the particles, if the particles have been attached to the substance,
    the analyzing device comprising:
    a sensing unit for sensing the particles on the binding surface, wherein the sensing unit is adapted to generate a sensing signal depending on the bound particles,
    a binding event determination unit for determining binding events from the generated sensing signal,
    a substance determination unit for determining the substance within the fluid based on the determined binding events.

In a further aspect of the present invention an analyzing device for cooperating with a binding device for determining a substance within a fluid is presented, wherein the binding device comprises:
    particles for being attached to the substance within the fluid,
    a binding surface for binding the particles, if the particles have been attached to the substance,
    the analyzing device comprising:
    a sensing unit for sensing the particles on the binding surface, wherein the sensing unit is adapted to generate a sensing signal depending on the bound particles,
    a binding event determination unit for determining binding events indicating a binding of a particle on the binding surface from the generated sensing signal,
    a substance determination unit for determining the substance within the fluid based on the determined binding events.

The analyzing device preferentially comprises a magnetic unit for attracting the particles, which are preferentially magnetic, to the binding surface and for pulling the particles away from the binding surface.

In a further aspect of the present invention a substance determining method for determining a substance within a fluid is presented, wherein the substance determining method comprises following steps:
    attaching particles to the substance within the fluid,
    binding the particles to a binding surface, if the particles have been attached to the substance,
    sensing the particles on the binding surface by a sensing unit, wherein a sensing signal is generated depending on the bound particles,
    determining binding events indicating a binding of a particle on the binding surface from the generated sensing signal by a binding event determination unit,
    determining the substance within the fluid based on the determined binding events by a substance determination unit.

In a further aspect of the present invention a binding method for cooperating with an analyzing method for determining a substance within a fluid is presented, the binding method comprising following steps:
    attaching particles to the substance within the fluid,
    binding the particles to a binding surface, if the particles have been attached to the substance,
    the analyzing method comprising following steps:
    sensing the particles on the binding surface by a sensing unit, wherein a sensing signal is generated depending on the bound particles,
    determining binding events indicating a binding of a particle on the binding surface from the generated sensing signal by a binding event determination unit,
    determining the substance within the fluid based on the determined binding events by a substance determination unit.

In a further aspect of the present invention an analyzing method for cooperating with a binding method for determining a substance within a fluid is presented, wherein the binding method comprises following steps:
    attaching particles to the substance within the fluid,
    binding the particles to a binding surface, if the particles have been attached to the substance,
    the analyzing method comprising following steps:
    sensing the particles on the binding surface by a sensing unit, wherein a sensing signal is generated depending on the bound particles,
    determining binding events indicating a binding of a particle on the binding surface from the generated sensing signal by a binding event determination unit,
    determining the substance within the fluid based on the determined binding events by a substance determination unit.

In a further aspect of the present invention an analyzing computer program for determining a substance within a fluid is presented, wherein the computer program comprises program code means for causing a substance determining apparatus as defined in claim 1 to carry out the steps of the analyzing method as defined in claim 12, when the computer program is run on a computer controlling the substance determining apparatus.

It shall be understood that the substance determining apparatus of claim 1, the binding device of claim 9, the analyzing device of claim 10, the substance determining method of claim 11, the above described binding method, the analyzing method of claim 12 and the analyzing computer program of claim 13 have similar and/or identical preferred embodiments as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

BRIEF DESCRIPTION OF THE DRAWINGS

In the following drawings:

FIG. 1 shows schematically and exemplarily a cross-section of a binding device,

FIG. 2 shows schematically and exemplarily a capillary structure of the binding device, FIG. 3 shows schematically and exemplarily a top view on the binding device.

DETAILED DESCRIPTION OF EMBODIMENTS

Figure 4:
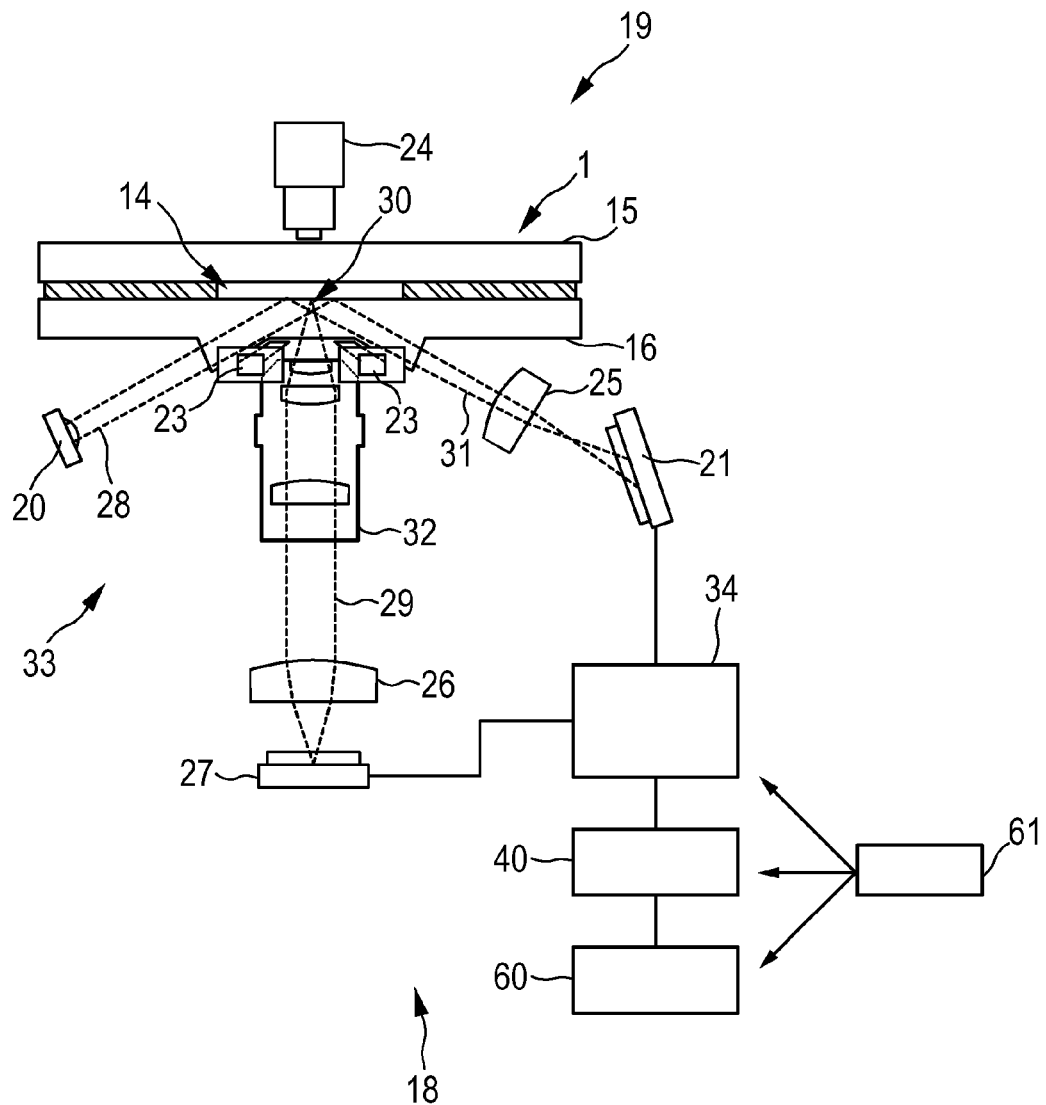
FIG. 4 shows schematically and exemplarily a substance determining apparatus comprising the binding device and an analyzing device.

FIG. 1 shows schematically and exemplarily a binding device 1 for binding a substance, which has to be determined within a fluid 3. The binding device 1 comprises a filter element 2 for filtering the fluid 3 and a capillary structure 5 for generating capillary forces. The capillary structure 5 is attached to the filter element 2 by using preferentially an adhesive. The capillary structure 5 is, in this embodiment, made of a double-sided tape which is adhesive on two sides.

The binding device 1 comprises a filtering location 6 at which the filter 2 is located and a sensing location 7 at which a substance within the fluid 3 is detectable, wherein the capillary structure 5 is formed such that the filtered fluid 3 is guided from the filtering location 6 to the sensing location 7 by capillary forces.

The capillary structure 5 comprises a collecting channel 8, which connects the filtering location 6 with the sensing location 7, and guiding channels 9 located at the filtering location 6, wherein the guiding channels 9 extend from an end of the connecting channel 8. In this embodiment the guiding channels 9 extend radially from the end 10 of the connecting channel 8. The capillary structure 5 is schematically and exemplarily shown in more detail in FIG. 2. FIG. 3 shows schematically and exemplarily a top view on the binding device 1 which is shown in a sectional view in FIG. 1.

The binding device 1 comprises a sensing cavity 14 which is located at the sensing location 7 and in which a substance of the fluid 3 is detectable. This sensing cavity 14 is formed by a first part 15 and a second part 16 of the binding device 1 together with the capillary structure 5. In addition, the first part 15 and the second part 16 form together with the capillary structure 5 the connecting channel 8. The first part 15 and the second part 16 are preferentially attached to each other via an adhesive, in particular, via the double-sided tape forming the capillary structure 5. The first part 15 and the second part 16 are plastics substrates which are injection molded and preferentially transparent to visible light. The first part 15 can be regarded as an upper substrate, closing element or cover element and the second part 16 can be regarded as a lower substrate or base element of the binding device 1. The first part 15 comprises a vent 39 for allowing a gas to leave the capillary structure 5.

In this embodiment, the filter element 2 is a blood separation filter and the binding device 1 forms a cartridge which is preferentially disposable. The binding device 1 is preferentially used in point-of-care diagnostics. The binding device 1 is preferentially adapted for detecting a low concentration biomarker in a sample of whole blood, in particular, in a finger prick sample of, for example, 25 µl. The sensing location 7 preferentially comprises an immunoassay. In particular, the sensing location 7 comprises a group 17 of particles for being attached to a substance within the fluid 3, wherein the group of particles mixes with the fluid 3, and the particles attach the substance within the fluid 3, if the fluid 3 is at the sensing location 7. The group 17 of particles can also be located between the sensing location 7 and the filtering location 6.

FIG. 4 shows schematically and exemplarily a substance determining apparatus 19 comprising the binding device 1 and an analyzing device 18. The binding device 1 has been inserted into the analyzing device 18. The analyzing device 18 comprises a sensing unit 33 for sensing the particles on the binding surface 30, wherein the sensing unit 33 is adapted to generate a sensing signal depending on the bound particles. The analyzing device 18 further comprises a binding event determination 34 for determining binding events indicating a binding of a particle on the binding surface 30 from the generating sensing signal, and a substance determination unit 40 for determining the substance within the fluid based on the determined binding events. Preferentially, the substance determination unit 40 is adapted to determine the amount and/or concentration of the substance within the fluid based on the determined binding events.

The substance determining apparatus 19 is a magnetic biosensor, wherein the particles are magnetic beads, i.e. nanoparticles, which label the substance by being attached to the substance. For attaching the substance the magnetic beads are functionalized with an attaching element that can be attached to the substance being, for example, a specific analyte molecule. In this embodiment, the attaching element is an antibody. However, the attaching element can also be a protein, DNA, aptamer et cetera.

The sensing unit 33 comprises a magnetic unit 23, 24 for attracting the magnetic particles to the binding surface 30 and for pulling the magnetic particles away from the binding surface 30. The magnetic unit comprises a horseshoe magnet 23 being preferentially in a planar arrangement at one side of the binding device 1, if the binding device is inserted into the analyzing device, and a second magnet 24 being arranged on the opposite side of the binding device 1, if the binding device is inserted into the analyzing device. The magnetic unit 23, 24 is a force applying unit for applying a force to the particles bound to the binding surface 30.

The sensing unit 33 is preferentially adapted such that the generated sensing signal is indicative of starting moments and ending moments of single binding events. In particular, the sensing unit 33 is adapted to generate images of the binding surface 30 at different times as the sensing signal, wherein an image shows at which positions on the binding surface 30 particles are bound at a time.

In this embodiment, the sensing unit 33 comprises a light source 20 being, for example, a light emitting diode or a laser for generating radiation 28 for being directed to the binding surface 30 for generating an evanescent field on the binding surface 30. The evanescent field on the binding surface 30 is influenced by the particles bound to the binding surface 30, thereby influencing a reflected light beam 31 comprising the light being total internally reflected at the cartridge surface, and a scattered light beam 29 comprising the light of the evanescent field scattered by the particles bound to the binding surface 30. The reflected light 31 is imaged by an objective 25 onto a first light detector 21 being preferentially a CCD camera. The scattered radiation is collected by a microscope objective 32 and imaged on a second detector 27 by an imaging lens 26. Also the second detector 27 is preferentially a CCD camera. The first detector 21 and the second detector 27 generate sensing signals which are provided to the binding event determination unit 34 for determining binding events indicating a binding of a particle on the binding surface 30, in particular, for determining lifetimes of the binding events from the generated sensing signal. The sensing signal of the first detector 21 is based on FTIR and the sensing signal generated by the second detector 27 is based on DFM.

At least one of the sensing signals of the first detector 21 and the second detector 27 forms images of the binding surface at different times showing at which positions on the binding surface particles are bound at the different times. The sensing unit can comprise elements for detecting the sensing signal of the first detector or the second detector only, i.e. the detection system for detecting the FTIR sensing signal or the detection system for detecting the DFM sensing signal can be omitted. In a preferred embodiment, the sensing unit only comprises the detection system for generating the DFM sensing signal based on the light of the evanescent field scattered by the particles bound to the binding surface.

In the following the generation of the sensing signals will shortly be described. If a beam of light reflects on the interface between a medium with a higher refractive index, for example the second part 16, and a lower refractive index, for example the fluid, there is a certain critical angle of incidence above which there is a situation of total internal reflection (TIR). The detection configuration (regarding refractive indices and angle of incidence) shown in FIG. 4 is such that there is total internal reflection of the incoming beam. Although the light is totally reflected in such a situation, there is still penetration of the light in a very thin layer of the medium with the low refractive index. This is called an evanescent field, the intensity of which decays exponentially in the low refractive index medium with a characteristic penetration depth of the order of the wavelength of the light. In practice the penetration depth is preferentially less than 0.5 micrometer. If magnetic particles are bound to the binding surface 30, the optical properties of this very thin first fluid layer of preferentially about 0.5 micrometer are changed leading to a reduction of the intensity of the reflected light beam. This is caused by absorption and scattering of the evanescent light (FTIR; frustrated total internal reflection). As a result the light intensity, and hence the signal, at the detector 21 decreases, whereas the light intensity, and hence the signal, at the detector 27 increases.

The binding event determination unit 34 is preferentially adapted to determine the lifetimes of binding events by determining the starting moments and the ending moments of single binding events at the different positions on the binding surface from the generated sensing signal. In particular, the binding event determination unit 34 is adapted to determine the starting moments and the ending moments by comparing temporally consecutive images of the binding surface generated at different times by the first detector 21 or the second detector 27. The lifetime generally depends on the kind of binding.

Figure 5:
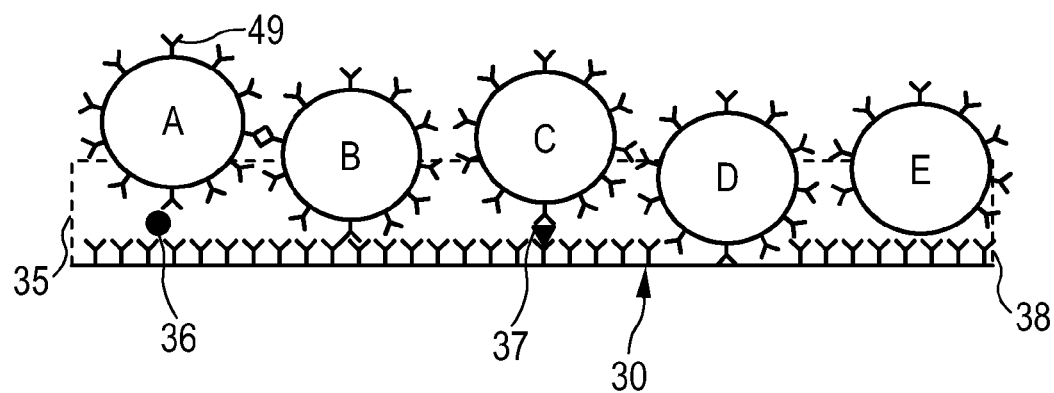
FIG. 5 shows schematically and exemplarily different kinds of binding to a binding surface.

FIG. 5 shows schematically and exemplarily different kinds of binding on the binding surface 30. In FIG. 5 the broken line 35 indicates schematically and exemplarily a height of the evanescent field which can be defined as a decay length $\zeta$ of the evanescent field. The particle indicated by A is specifically bound to the binding surface 30 via the attaching element 49, the substance 36 and the binding element 38. The particle B does not form a normal sandwich like the particle A, but is bound to the binding surface 30 via the attaching element 49 and the binding element 38, i.e. without a sandwiched substance.

The particle C is bound to the binding surface 30 via the attaching element 49, an element 37 not being the substance to be determined, i.e. not being the analyte, and the binding element 38. The particle D is directly bound to an exposed area on the binding surface 30 via the attaching element 49. This means, the binding surface 30 comprises the binding elements 38 for forming a normal sandwich as shown in FIG. 5 for the particle A. These binding elements 38 also bind particles B, C and E in the example shown in FIG. 5. However, the particle D is directly bound to the binding surface 30 via the attaching element 49.

An exposed area of the particle E is bound to the binding surface 30 directly via the binding elements 38, i.e. the particles comprise attaching elements 49 for attaching the substance, wherein the particles A, B, C, D are bound to the binding surface 30 via the attaching elements 49 of the respective particle. However, the particle E is not bound to the binding surface 30 via the attaching elements 49, but an exposed area of the particle E is attached to the binding surface 30 via the binding element 38.

In FIG. 5, only the particle A forms a normal sandwich. The particle A is therefore specifically bound to the binding surface 30. The other particles B, C, D, E do not form a normal sandwich and are therefore non-specifically bound to the binding surface 30.

These different kinds of binding are generally related to different lifetimes. Thus, by determining the lifetimes of binding events the kind of the respective binding can be determined.

A non-specific binding is preferentially any binding that is not dependent on the presence of the substance, i.e. on the presence of the specific analyte that is to detect in the sample fluid. FIG. 5 illustrates differences between specific and non-specific binding for a sandwich immunoassay. However, also other kinds of assay can comprise specific and non-specific binding and the substance determining apparatus can also be used to determine specifically bound particles if another assay is chosen for determining the substance in the fluid.

The lifetimes cannot only be used for distinguishing between specific and non-specific binding. The different lifetimes can also be used to determine which kind of particle is bound, because the lifetime generally also depends on the kind of particle which is bound to the binding surface.

The sensing unit 33 is adapted such that sensing signals, i.e. signal changes, caused by single particles can be distinguished using the scattered light 29 collected by the microscope objective 32 and imaged onto the second light detector 27 by the imaging lens 26. The second light detector 27 comprises a two-dimensional detection surface 30 for generating images of the binding surface at different times. If at a certain position in the image a bound particle is detected and if at this position a particle was not detected in a temporally preceding image, a starting moment of a binding event is detected, and, if at this position in a later image the bound particle has disappeared, the ending moment of this binding event can be determined. Differences between the ending moments and the starting moments define the lifetime of the respective binding events. Since these binding events and the corresponding lifetimes are determined over some time and among the binding surface, a large amount of binding events and corresponding lifetimes can be determined by the binding event determination unit 34. The binding event determination unit 34 can form a histogram of the lifetimes and determine the substance within the fluid based on the histogram.

The substance determining apparatus 19 is preferentially adapted to provide a binding phase and a washing phase. In the binding phase the force applying unit forces the particles towards the binding surface, in order to allow the particles to be bound to the binding surface, and away from the binding surface to remove unbound particles in an alternating way. In the following washing phase the force applying unit applies a force to the particles, which urges the particles only away from the binding surface, thereby washing unbound particles away from the binding surface and putting the bindings between bound particles and the binding surface under stress. The stress can lead to a release even of bound particles.

The histogram can be determined in the binding phase or in the washing phase. If the histogram shall be determined in the binding phase, images of the binding surface are provided by the second detector at least at the times at which the unbound particles have been pulled away from the binding surface in the binding phase. Preferentially, consecutive images generated while the unbound particles are pulled away from the binding surface in the binding phase are compared for determining the lifetime of the bindings. If a particle is visible at a certain position in a first image and at the same position not in a preceding image, the time of a starting moment can be detected. If at a certain position with a second image a particle is visible and if at the same certain position in a subsequent image a particle is not visible, the time of an ending moment can be determined. The determined starting and ending times are used for determining lifetimes of single binding events, wherein a histogram of these lifetimes is formed. The substance determining apparatus is preferentially adapted to determine a part of the histogram depending on a temporal behavior of the histogram being indicative of a certain kind of binding and to determine the substance within the fluid based on the determined part of the histogram being indicative of the certain kind of binding. Preferentially, a linear combination of exponential decay curves with different time constants is fitted to the histogram, wherein the time constants of the exponential decay curves define the temporal behavior of the histogram. The substance determining apparatus preferentially comprises assignments between fitted time constants of the exponential decay curves and certain kinds of bindings, wherein the fitted exponential decay curves having fitted time constants, which correspond to a desired certain kind of binding, is preferentially determined as the part of the histogram being indicative of the certain kind of binding. In an embodiment, the substance determination unit 40 is adapted to provide a fitting curve comprising a combination of a) a first product of a first number of binding events with a predefined lifetime and a first exponential decay fitting curve having a first time constant and b) a second product of a second number of binding events with the predefined lifetime and a second exponential decay fitting curve having a second time constant. The substance determination unit 40 is further adapted to fit the fitting curve to the histogram, wherein the first number of binding events, the first time constant, the second number of binding events and the second time constant are fitting parameters, and to determine the part of the histogram being indicative of the certain kind of binding as the fitted first exponential decay fitting curve and/or the second fitted exponential decay fitting curve, if the corresponding time constants are indicative of the desired certain kind of binding.

In another embodiment, the substance determination unit can be adapted to modify the histogram by differentiating the histogram with respect to the lifetime and multiplying the differentiated histogram with the lifetime, wherein extremal lifetimes at which the modified histogram has an extremum are determined and wherein the substance is determined depending on the determined extremal lifetimes. In particular, time constants are determined as the inverse of the determined extremal lifetimes, a fitting curve comprising combinations of products of numbers of binding events with a predefined lifetime and exponential decay fitting curves having the determined time constants are provided, and the fitting curve is fitted to the histogram, wherein the number of binding events with the predefined lifetime are fitting parameters. The substance is determined depending on at least one of the products of fitted numbers of binding events with a predefined lifetime and the exponential decay fitting curve with the determined time constant, if the determined time constant is indicative of the desired kind of binding. As already mentioned above, the substance determining apparatus can be adapted to apply a force to the particles by the force applying unit 23, 24 for putting bindings between the particles and the binding surface under stress, while sensing the particles. The time constants generally depend on the force applied to the particles for putting the bindings under stress. Preferentially, the force is applied such that the differences between the time constants are increased, thereby improving the quality of determining the time constants. For example, the force applying unit 23, 24 can be adapted to apply a force to the particles, which urge the particles in a direction away from the surface, while sensing the particles, in order to increase the differences between the time constants.

The different time constants characterize different kinds of binding. As already explained above with reference to FIG. 5, different kinds of binding are, for example, a first kind of binding being a specific binding and a second kind of binding being a non-specific bind. Further kinds of binding can be bindings of different kinds of particles, which belong to different substances, to the binding surface. Preferentially, the substance determination unit is adapted to determine a first part of the histogram related to specifically bound particles and a second part of the histogram related to non-specifically bound particles depending on the time constants which have been determined by fitting a linear combination of exponential decay curves to the histogram. The substance determination unit 14 is then preferentially further adapted to determine the amount and/or concentration of the substance within the fluid based on the determined first part of the histogram related to specifically bound particles.

Figure 6:
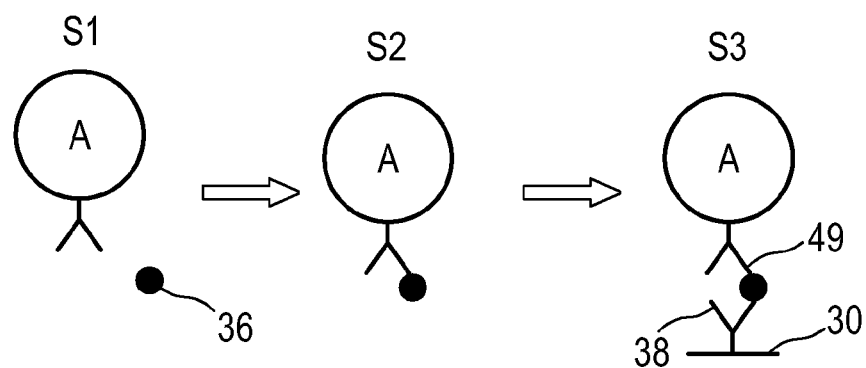
FIG. 6 shows schematically and exemplarily a specific binding process.

FIG. 6 illustrates schematically and exemplarily a normal specific sandwich immunoassay.

The particle A with the attaching elements 49 is mixed with the fluid comprising the substance 36 (step S1). Then, the attaching element 49 attaches the substance 36 (step S2), and the particle A with the attaching element 49 and the attached substance 36 specifically bounds to the binding surface 30 via a binding element 38 (step S3).

As preferentially performed in all described embodiments, after the fluid has mixed with the particles for allowing the particles to attach the substance within the fluid, the particles are attracted to the binding surface for allowing the particles to be bound on the binding surface in a binding phase. In a following washing phase, the particles which are not bound to the binding surface are pulled away from the binding surface. As already mentioned above, in the binding phase alternating forces can be applied to the particles pointing towards the binding surface and pointing away from the binding surface. The sensing signal can be generated in the binding phase, in which an alternating force may be applied to the particles, and/or in the washing phase.

If several kinds of binding are present, the several kinds of binding generally relate to different reaction constants and, thus, to different time constants. In an embodiment, a first kind of binding is a binding of a specifically bound particle and a second kind of binding is a binding of a non-specifically bound particle. Both, the specifically bound particles and the non-specifically bound particles contribute to the histogram. The substance determining apparatus is preferentially adapted to determine the part of the histogram caused by the specifically bound particles only.

Figure 7:
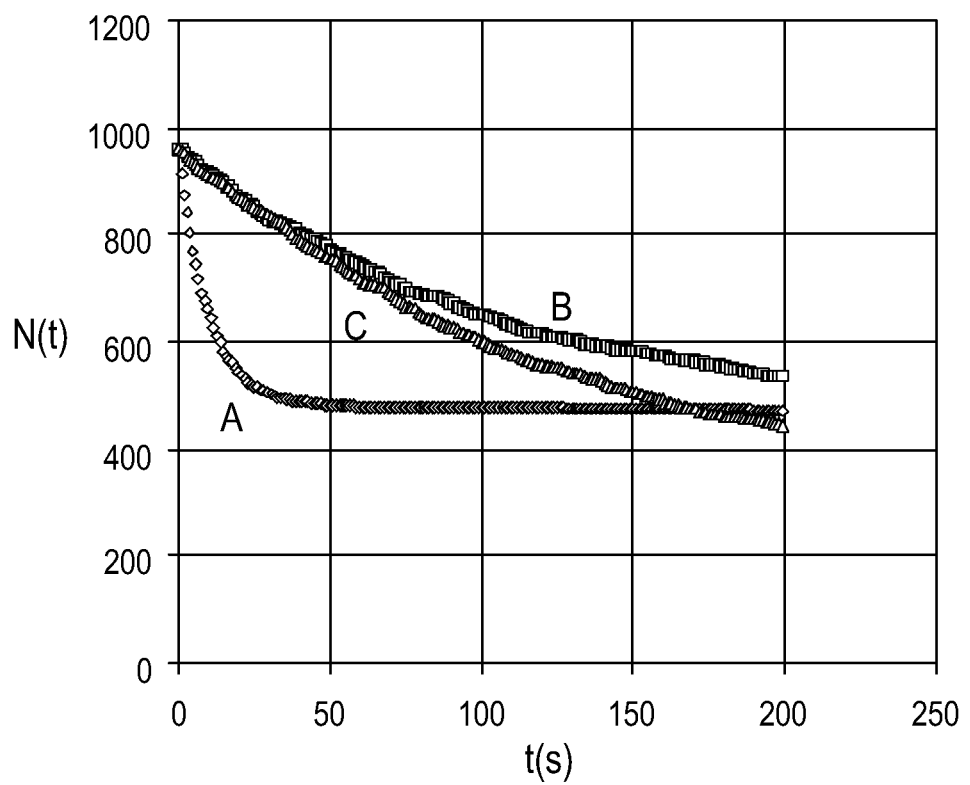
FIG. 7 shows schematically and exemplarily several histograms which correspond to two different kinds of binding.

In the following the chemical reaction constant of specifically bound particles is denoted by $k_{off,chem,spec}$ and the chemical reaction constant of non-specifically bound particles is denoted by $k_{off,chem,non-spec}$, wherein the chemical reaction constant defines the time constant, if a force is not applied to the particles. If there is a large difference between these two reaction constants, for example, a difference of about three orders of magnitude, and if a part of the histogram caused by one of the specifically bound particles and the non-specifically bound particles relates to a relatively large signal change within the sensing time, the decrease of the histogram consists of two exponential decays with significantly different time constants. This allows the binding determination unit to distinguish the part of the histogram caused by specifically bound particles from the part of the histogram caused by non-specifically bound particles in a simple way. For example, if the non-specific chemical reaction constant is much larger than the specific chemical reaction constant such that the non-specifically bound particles are released very fast at the beginning of the sensing time, the part of the histogram caused by specifically bound particles can immediately be determined from the level of the tail of the histogram at the end of the sensing time. A corresponding histogram is shown in FIG. 7 as curve indicated by A. The inflection point of the curve indicated in FIG. 7 by A could be used to terminate the particle release of the non-specifically bound particles.

FIG. 7 shows schematically and exemplarily several histograms which correspond to specifically bound particles and non-specifically bound particles having different reaction constants, i.e. different time constants. The histogram indicated by A corresponds to a difference of the reaction constants of three orders of magnitude, the histogram indicated by B corresponds to a difference of the reaction constants of two orders of magnitude and the histogram indicated by C corresponds to a difference of the reaction constants of one order of magnitude.

It should be noted that the histograms shown in FIG. 7 do not change over time like, for example, equalizer displays on sound equipment. The temporal behaviour of the histogram is defined by the time-dependent decay shown in FIG. 7.

If the difference between the specific chemical reaction constant $k_{off,chem,spec}$ and the non-specific chemical reaction constant $k_{off,chem,non-spec}$ is equal or less than two orders of magnitude, the distinction between the two exponential functions is less clear. The curves look more smooth and it is almost impossible to tell by eye that there are two distributions present. A fitting procedure is preferred to determine a fraction f of the histogram caused by specifically bound particles. In this case the histogram can be described by following equation:

$$N(t)=N_0 \cdot (f \cdot e^{-k_{off,chem,spec} \cdot t} + (1-f) \cdot e^{-k_{off,chem,non-spec} \cdot t}). \quad (1)$$

In an embodiment, the binding determination unit is preferentially adapted to fit equation (1) to a histogram, wherein the fitting parameters are f, $k_{off,chem,spec}$ and $k_{off,chem,non-spec}$, if an external force is not applied to the particles for putting the bindings under stress. The substance determination unit then determines the amount or concentration of the substance within the fluid based on the specific part $N_{spec}(t)$ of the histogram defined by following equation:

$$N_{spec}(t)=N_0 \cdot f. \quad (2)$$

The variable $N_0$ indicates the histogram at the beginning of a sensing time, i.e. at t=0.

As already mentioned above, during the sensing time a force can be applied to the bound particles, in order to put the bindings between the particles and the binding surface under stress. This increases the reaction constants, wherein the forces are preferentially applied such that a change of the histogram caused by the most weakly bound particles is detectable during the sensing time. Preferably, the forces are applied such that the desorption of the non-specifically bound particles is mainly within the sensing time, while the desorption of the specifically bound particles is mainly outside the sensing time. The histogram N(t) as a function of time can then be described by following equation:

$$N(t)=N_0 \cdot (f \cdot e^{-k_{off,chem,spec} \cdot c(F) \cdot t} + (1-f) \cdot e^{-k_{off,chem,non-spec} \cdot c(F) \cdot t}). \quad (3)$$

As already mentioned above, depending on the kind of force applied to the particles, the force F can be independent of the time or the force F can depend on the time. In both cases the binding determination unit can determine the force F and the correction factor c(F). The binding determination unit is then preferentially adapted to fit equation (3) to the generated histogram, wherein the fitting parameters are f, $k_{off,chem,spec}$ and $k_{off,chem,non-spec}$, i.e. f, and the corrected time constants being the inverse of the chemical reaction constants. The binding determination unit is then further adapted to determine the part of the histogram caused by particles bound to the binding surface via a specific binding in accordance with equation (2), and the substance determination unit is adapted to determine the amount and/or concentration of the substance within the fluid based on this determined part of the histogram. For determining the amount and/or concentration of the substance the substance determination unit preferentially comprises assignments between the part of the histogram caused by specifically bound particles and the amount and/or concentration of the substance within the fluid. These assignments can be determined by performing calibration procedures with known amounts and/or concentrations of specifically bound particles. The assignments can be stored in the substance determination unit in tabular form or as functions.

The fitted time constants can be compared with time constants which are known to relate to certain kinds of binding. For example, experiments carried out on samples which only contain specific or non-specific bindings can be used to determine the time constants for those bindings. For example, only non-specific bindings can be made on the binding surface by not introducing the substance in the fluid, and only specific bindings can be made by using high concentrations of the substance within the fluid, at which the amount of non-specific bindings is negligible.

By stressing the bonds by means of an external force the release rate can be increased. The combination of the chemical reaction constant $k_{off,chem}$ and an external force F to stress the bonds results in a new effective release rate $k_{off,eff}$. If the external force F is known, the chemical reaction constant $k_{off,chem}$ can be calculated from the effective $k_{off,eff}$ in accordance with following equation:

$$k_{off,eff} = k_{off,chem} \cdot c(F), \quad (4)$$

where c(F) is a correction factor which depends on the magnitude of the force. The function c(F) is preferentially a simple linear or exponential function with only one parameter, wherein the parameter can be estimated or determined by means of calibration. The calibration can be performed by applying known forces to the particles, determining the effective reaction constant $k_{off,eff}$ and by dividing the determined effective reaction constant by a known chemical reaction constant $k_{off,chem}$. The reaction constant is preferentially defined as the inverse time constant of the exponential decay of the histogram.

In particular, the correction factor c(F) can be expressed by following equation:

$$c(F) = e^{\beta F}, \quad (5)$$

wherein β is a proportionality factor being a constant which can experimentally be determined for the respective kind of binding. Preferentially, the force applied to each particle is determined and an average force F is determined by averaging the forces determined for the bound particles. This average can be a weighted average, wherein the forces receive the same weight or the forces receive different weights depending on the magnitude of the respective force. For example, a larger force can receive a weight being larger than the weight of a smaller force.

The magnetic force F exerted onto a particle by the magnetic field and the magnetic field gradient can be determined by following equation:

$$\vec{F} = (\vec{m}(\vec{B}) \cdot \vec{\nabla}) \cdot \vec{B}, \quad (6)$$

wherein in $\vec{m}(\vec{B})$ is the field-dependent magnetic moment of the particle and $\vec{B}$ is the applied magnetic induction. The magnetic field and the magnetic field gradient are preferentially adapted such that a force is generated for pulling the particles vertically with respect to the binding surface away from the binding surface or attracting the particles vertically towards the binding surface. Since the magnetic properties of the particles and the magnetic field are known, the vertical force on the particles can be calculated. The magnetic properties of the particles can be determined by means of a Vibrating Sample Magnetometer (VSM) measurement and the magnetic field and magnetic field gradient can be determined from finite-element calculations and calibrated by means of a magnetic field sensor.

The force applying unit 23, 24 is, in this embodiment, a magnetic unit for attracting the particles to the binding surface or for pulling the particles in a direction away from the binding surface. However, magnetic forces can also be applied to change the orientation of the particles for putting the bindings under stress.

This can be performed due to non-ideal magnetic properties, because the magnetic moment of an ideally superparamagnetic particle would always align with the field, thus making induction of an orientation change impossible. Non-ideal magnetic properties are, for example, a small permanent moment, magnetic grains with relatively long relaxation times or magnetic anisotropy. The force applying unit can be preferentially adapted to apply an orientation change to the bound particles such that the height of the bound particles, i.e. the distance of the bound particles to the binding surface, is modified. Thus, by applying an orientation change to the bound particles the distance between the particles bound to the binding surface and the binding surface can be modified for modifying the stress apparatus to the bindings. The particles can be magnetic particles having a diameter between 500 nm and 1000 nm and can be composed of a combination of polystyrene and a magnetic material.

Figure 8:
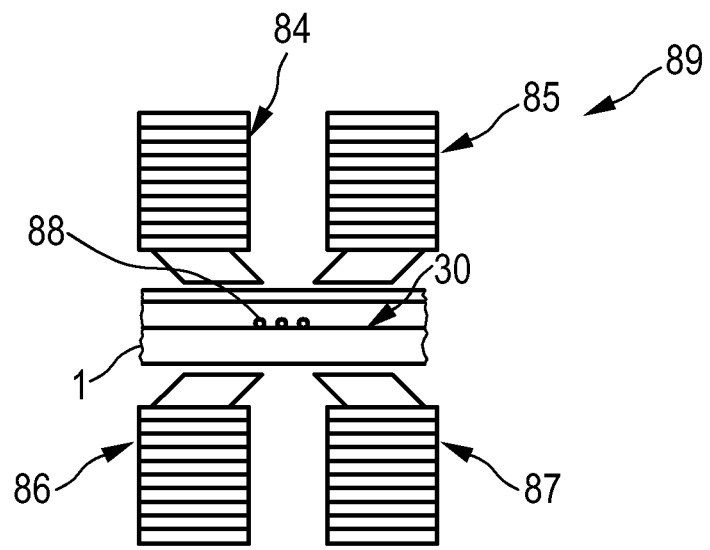
FIG. 8 shows schematically and exemplarily a force applying unit for applying magnetic forces to particles such that the orientation of the particles is modified.

FIG. 8 shows schematically and exemplarily a force applying unit 89 for applying magnetic forces to the magnetic particles 88 such that the orientation of the magnetic particles can be modified, thereby modifying the height of the magnetic particles 88 bound to the binding surface 30. The force applying unit 89 comprises four electromagnets 84, 85, 86, 87 for applying the magnetic field in the desired direction to the magnetic particles 88.

The force applying unit 89 is adapted to magnetically orient the magnetic particles 88, which are, in this embodiment, non-ideally superparamagnetic particles, for putting the bindings under stress. A bound particle that rotates in a magnetic field, which can be regarded as an out-off-plane rotation, changes its height above the binding surface and thereby puts its binding under stress.

It should be noted that the force applying unit 89 shown in FIG. 8 is a part of an analyzing device for cooperating with the binding device 1, i.e. the cartridge 1, for determining a substance within a fluid. Thus, the force applying unit 89 shown in FIG. 8 can be used instead of or in addition to the magnetic unit 23, 24 in the substance determining apparatus described above with reference to FIG. 4.

Although in the above described embodiments force has been applied to the particles bound to the binding surface by magnetic forces, in other embodiments, in addition or alternatively, the force applying unit can be adapted to apply another kind of force to the particles bound to the binding surface. For example, the force applying unit can be adapted to apply a fluidic force or an electrostatic force to the particles bound to the binding surface.

In an embodiment, the force applying unit is adapted to use electrostatic forces to push particles bound to the binding surface away from the binding surface for putting the bindings under stress. This can be performed by exchanging the fluidic buffer in a fluidic wash step, while the particles remain bound to the binding surface.

Both, the particles and the binding surface, have an electrostatic surface charge in the fluid due to absorption of ions from the fluid or dissociation of surface groups on the surfaces. Typically, in biosensor environments, the surface charge is negative for both, the particles and the binding surface, leading to a natural repulsion between particles and binding surface. Ions in the fluid can screen the charge of both surfaces, thereby decreasing the repulsion.

The layer over which screening takes place is called the double layer. The inverse double layer thickness κ, correlated to the Debye-Hueckel length $\lambda_D$ ($\lambda_D = \kappa^{-1}$), is given by:

$$\kappa = \sqrt{\frac{2000 e^2 N_A I_C}{\varepsilon_0 \varepsilon_r k_B T}}, \quad (7)$$

where e is the elementary charge, $N_A$ Avogadro's number, $I_C$ the ionic strength of the fluid, $\in_0$ the dielectric permittivity of free space, $\in_r$ the relative permittivity of the fluid and $k_B T$ the thermal energy.

The electrostatic interaction energy between a particle and a surface depends on the inverse double layer thickness and is given by:

$$E_{es} = ZR \cdot \exp(-\kappa h) \tag{8}$$

with R the particle radius, h the distance between the particle (bottom) and the surface and Z given by:

$$Z = 64\pi\varepsilon_0\varepsilon_r \left(\frac{k_B T}{e}\right)^2 \tanh\left(\frac{ze\psi_{particle}}{4k_B T}\right) \tanh\left(\frac{ze\psi_{surface}}{4k_B T}\right). \tag{9}$$

Here z is the electrolyte valence, and $\psi_{particle}$ and $\psi_{surface}$ the surface potentials of respectively the particle and the surface. The electrostatic force between a particle bound to the binding surface and the binding surface depends therefore on the ionic strength of the buffer and can be increased by decreasing the ion concentration in the fluid. Thus, by modifying the ion concentration in the fluid, stress applied to the bindings between the particles bound to the binding surface and the binding surface can be modified. The force applying unit can therefore be adapted such that the ion concentration in the fluid can be modified. The ion concentration can, for example, be changed by inserting a new fluid in the binding device such that the new fluid is present on the binding surface. For example, the analyzing device can be adapted to fill a new fluid into the binding device, which is preferentially a cartridge, along the same way which has been used for transferring the original fluid like the blood to the binding surface.

Generally, also the Van der Waals interaction is present between the particles bound to the binding surface and the binding surface. The Van der Waals interaction can be expressed by following equation:

$$E_{vdw} = -\frac{1}{6} A_{132} \left[\frac{R}{h} + \frac{R}{h+2R} + \ln\left(\frac{h}{h+2R}\right)\right] \tag{10}$$

with $A_{132}$ the Hamaker constant of a particle of material 1 on a surface of material 2 in a fluid of material 3. The value of the Hamaker constant is usually around a few $k_B T$, and can be positive (attractive) or slightly negative (repulsive, mainly due to the presence of proteins on the surfaces). The force between the particles bound to the binding surface and the binding surface is the negative gradient of the respective interaction term, i.e. e.g. the negative gradient of $E_{es}$ and $E_{vdw}$.

By varying the Hamaker constant, for example, by exchanging the fluid, the Van der Waals interaction between the bound particles and the binding surface and, thus, the stress applied to the bindings between the bound particles and the binding surface can be modified.

Referring again to FIG. 4, the substance determination apparatus 19 is comprised of the binding device 1 and the analyzing device 18. The binding device 1 is, in this embodiment, a cartridge including the particles and the binding surface and being adapted to receive the fluid 3. The analyzing device 18 can be regarded as a reader and includes the sensing unit 33, the binding event determination unit 34 and the substance determination unit 40. The binding device 1 is a disposable device and the analyzing device 18 is a re-useable device.

The analyzing device 18 further comprises an output unit 60 for outputting a value indicating the amount or concentration of the substance within the fluid. The output unit 60 is preferentially a display. The analyzing device 18 further comprises a control unit 61 for controlling the sensing unit 33, the binding event determination unit 34, the substance determination unit 40 and the output unit 60.

The substance determination unit is preferentially adapted to determine which part of the histogram relates to specifically bound particles having attached the substance depending on the temporal behavior of the histogram, wherein the amount or concentration of the substance within the fluid is determined based on this determined part.

As already mentioned above, the binding device 1 is preferentially a cartridge for receiving a fluid like blood, saliva or urine, for filtering the fluid and for transferring the filtered fluid to the sensing site of the cartridge. The cartridge is disposable and is adapted for single use only. The analyzing device 18 is adapted to be used several times with different cartridges. Thus, a fluid 3 like blood, saliva or urine is put on the filter element 2 of the binding device 1, the fluid 3 is filtered and the filtered fluid is transferred to the sensing location 7. The binding device 1, i.e. in this embodiment the cartridge, is arranged in the analyzing device 18 and a substance within the fluid 3 at the sensing location is analyzed by the analyzing device 18. After the binding device 1 has been used, it is preferentially discarded, whereas the analyzing device 18 is used for a next analyzing procedure.

Figure 9:
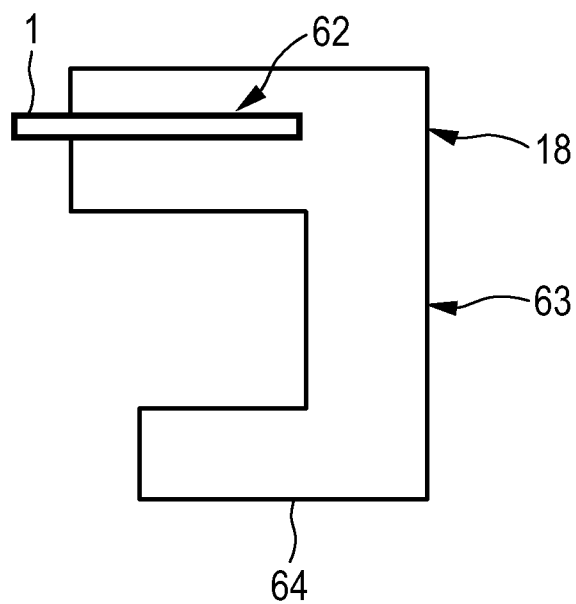
FIG. 9 shows schematically and exemplarily a binding device introduced into an analyzing device.

The several units of the analyzing device 18 are preferentially arranged within a casing 64, which is schematically and exemplarily shown in FIG. 9 and which can comprise a grip part 63 for allowing a user to hold the analyzing device 18 in the hand while analyzing the substance in the fluid. The casing 64 comprises a receiving section 62 for receiving the binding device 1. In other embodiments, the casing 64 can have another shape.

The several units of the analyzing device 18 can also be arranged within a casing not being a handheld casing. For example, the casing of the analyzing device can be adapted to stand on a table or the like.

Figure 10:
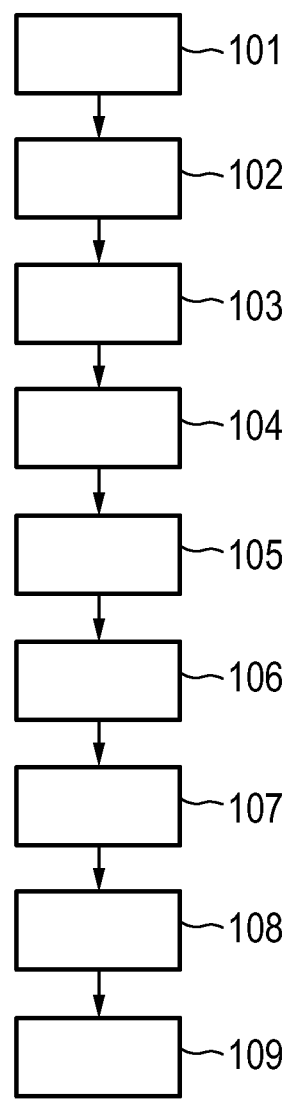
FIG. 10 shows a flowchart exemplarily illustrating a substance determining method for determining a substance in a fluid.

In the following a substance determining method for determining a substance within a fluid will exemplarily be described with reference to a flowchart shown in FIG. 10.

In step 101, a fluid sample, in particular, a blood sample, is arranged on the filter element 2.

In step 102, the fluid is filtered by the filter element 2, and in step 103 the filtered fluid is transferred to the sensing location 7 by capillary forces generated by the connecting channel and the guiding channels of the capillary structure.

Before, while or after performing steps 101 to 103 the binding device 1 has been introduced into the analyzing device 18. At the sensing location 7 magnetic particles coated with a specific antibody that attaches to a target molecule, i.e. the substance, present in the fluid are located. They mix with the filtered fluid, and the magnetic particles with the specific antibody attach to the target molecules within the fluid in step 104.

In step 105, the magnetic unit is controlled such that the magnetic particles at the sensing location 7 are forced onto the binding surface 30 in a binding phase. The magnetic particles with the attached target molecules bind to the binding surface 30 and in step 106, in a washing phase, the magnetic unit is controlled such that magnetic forces urge the magnetic particles away from the binding surface 30. This removes unbound particles from the binding surface and puts the bindings under stress. While the bindings are put under stress, a temporal sensing signal is generated depending on the bound particles. The temporal sensing signal is, for example, a DFM signal generated by the second detector 27.

The sensing signal is preferentially a temporal sequence of images of the binding surface, wherein an image shows at which positions on the binding surface particles are bound.

The images are preferentially two-dimensional images of the binding surface, which have been generated by detecting evanescent light from the binding surface, which has been scattered by the particles bound to the binding surface.

In step 107, the binding event determination unit determines binding events indicating a binding of particles on the binding surface, in particular, lifetimes of the binding events, from the generated sensing signal. In particular, the binding event determination unit determines the starting moments and the ending moments of single binding events at the different positions within the image by comparing temporally consecutive images.

In another embodiment, the sensing signal and binding events, in particular, lifetimes of binding events, can also be determined in the binding phase, In this case, in the binding phase the magnetic unit provides forces for urging the magnetic particles alternately towards the binding surface and away from the binding surface, in order to allow the sensing unit to determine a sensing signal being indicative of starting moments and ending moments of binding events as described above, in particular, starting moments and ending moments are preferentially determined based on images detected while particles are forced away from the binding surface in the binding phase. Preferentially, an image is generated in the binding phase, when the particles are forced away from the binding surface, then the particles are forced towards the binding surface, and then a further image is generated, while the particles are forced away from the binding surface. The image and the further image are compared, in order to determine starting moments and ending moments of binding events. In step 108, the substance determination unit determines the substance, in particular, the amount and/or concentration of the substance, within the fluid based on the determined binding events, in particular, the lifetimes of the binding events. In a preferred embodiment, exponential decay curves are fitted to a histogram of the lifetimes for determining a part of the histogram being indicative of a certain kind of binding, in particular, being indicative of a specific kind of binding. The substance determination unit is then preferentially adapted to determine the substance within the fluid based on the determined part of the histogram being indicative of the certain kind of binding. The determined substance, in particular, the determined amount and/or concentration of the substance, within the fluid is preferentially shown on the output unit 60 in step 109.

Steps 101 to 105 can be regarded as the steps of a binding method, and steps 106 to 109 can be regarded as the steps of an analyzing method.

Although in the above described embodiments a linear combination of exponential decay curves having certain time constants being indicative of certain kinds of binding has been fitted to the particle release curve for determining a part of the particle release curve caused by particles bound to the binding surface via a predefined kind of binding, this part of the particle release curve can also be determined by using another fitting procedure. Generally, the substance determination unit can be adapted to provide a first predefined fitting release curve having a first temporal behaviour being indicative of a first kind of binding and a second predefined fitting release curve having a second temporal behaviour being indicative of a second kind of binding. The substance determination unit is preferentially further adapted to fit the first predefined fitting release curve and the second predefined fitting release curve to the determined particle release curve by fitting a linear combination of the first predefined fitting release curve and the second predefined fitting release curve to the determined particle release curve, wherein one of the fitted first predefined release curve and the fitted second predefined release curve is determined as the part of the particle release curve caused by particles bound to the binding surface via a predefined kind of binding. In an embodiment, the first predefined fitting release curve is a specific calibration curve having a specific temporal behaviour being indicative of a specific binding and the second predefined fitting release curve is a non-specific calibration curve having a non-specific temporal behaviour being indicative of a non-specific binding. A preferred fitting procedure can be described by following equation:

$$N(t)=f*g_{spec}(t)+(1-)*g_{nonspec}(t). \quad (11)$$

In equation (11) $g_{spec}(t)$ indicates a specific calibration curve and $g_{nonspec}$ indicates a non-specific calibration curves. By performing the fitting procedure, the fraction f of specifically bound particles multiplied with the specific calibration curve can be regarded as the determined substance within the fluid, which has been determined based on the specific part of the particle release curve, or a concentration or an amount of the substance within the fluid can be determined based on the product of the fraction f and the specific calibration curve as the determined substance within the fluid.

The calibration curves can be defined either as real measured curves, for example, as a table with measured values, or as a parametric curve in which the parameters are determined by fitting the parametric curve to the measured curves. A parametric curve can be any model which describes the measured data such as a polynomial, a Fourier series, a linear superposition of exponentially decaying signals et cetera. In particular, a specific calibration curve can be determined, if only specifically bound particles are present, and a non-specific calibration curve can be determined, if only non-specifically bound particles are present.

In a further embodiment, a number of particle release curves is determined for known substance concentrations, wherein these measured particle release curves are regarded as concentration calibration curves. When determining a particle release curve with unknown concentration, the concentration can be determined from interpolation using the concentration calibration curves with known substance concentrations. As in the previous embodiment, the particle release curves of substances with known concentration can be parameterized using a certain mathematical function, yielding a set of parameter values at a certain concentration. Next, the release curve of the unknown substance is measured and parameterized using the same mathematical function, resulting in a set of parameters. Via interpolation of one or more of those parameters using the parameters of the parameterized concentration calibration curves, the unknown concentration can be determined. The above mentioned calibration curves can be arbitrary mathematical models which do not have any relation with the real physical or chemical model. However, the mathematical models could also describe the reality in a more accurate way, as might be the case with linear superposition of exponential decaying functions. In this case also physical or chemical parameters like time constants or reaction constants can be extracted from the fitting. Such a fitting of a linear superposition of exponential decaying functions to the determined particle release curve is described above in more detail.

Although in the above described embodiments the substance, i.e. e.g. the concentration, amount or a chemical property of the substance, has been determined based on lifetimes of binding events, in other embodiments, the substance can also be determined based on another characteristic of the binding events. For example, a particle arrival rate can be determined as a number of transitions from an unbound state to a bound state and a reaction constant $k_{on}$ can be determined from the particle arrival rate. In addition or alternatively, the chemical reaction constant $k_{off}$ can be determined based on a particle desorption rate being the number of transitions from a bound state to an unbound state per temporal unit. The concentration, amount or a chemical property of the substance within the fluid can be determined based on the chemical reaction constants $k_{on}$ and/or $k_{off}$. The particle arrival rate is preferentially determined in the binding phase and the particle desorption rate is preferentially determined in the binding phase and/or in the washing phase.

The substance determining apparatus is preferentially a magnetic biosensor that can be used to correct for non-specific binding. The substance determining apparatus is preferentially based on nanoparticles that can be actuated with electro-magnetic fields. The nanoparticles are preferentially magnetic beads which are functionalized with antibodies that can bind a specific analyte molecule. The beads are attracted to the binding surface, where the number of bound beads is directly or inversely related to the amount of analyte molecules present in the fluid sample. The beads are then preferentially detected by using a technique that is more sensitive to beads that are close to the binding surface than to beads that are more far away from the binding surface. The substance determining apparatus uses preferentially the above described FTIR technique and/or DFM technique. Using these techniques, the sensitivity to the nanoparticles decreases exponentially with an increasing distance from the surface. Generally, if the distance between the particles and the binding surface is larger, the corresponding sensing signal will be smaller. However, the sensing signal can also be defined such that a particle being close to the binding surface generates a smaller signal then a particle being more far away from the binding surface.

The binding device can be an optical cartridge being a carrier of a bioassay comprising particles being optical labels, preferably microscopic super-paramagnetic labels providing optical contrast by means of scattering and/or fluorescence.

Although in the above described embodiments total internal reflection has been used for inducing the evanescent field, in other embodiments other techniques can be used for inducing the evanescent field, for example, grating coupling or waveguide coupling can be used.

Although in the above mentioned embodiment described with reference to FIG. 4, a microscope objective 32 has been used, in other embodiments another objective lens for collecting and imaging of photons can be used. This objective lens is positioned at the bottom side of the binding device, underneath the horseshoe actuation magnet 23. The photons from the optical labels are transmitted through an air gap in between the two horseshoe magnets 23, before they are captured by the objective lens. The objective lens has a numerical aperture allowing imaging the individual optical labels onto the second light detector 27 being, for example, a CCD camera.

The substance determining apparatus is preferentially adapted to allow to determine the fraction of non-specifically bound particles from an ensemble of particles.

Although in the above described embodiments the substance determining apparatus comprises means for generating FTIR sensing signals and DFM sensing signals, in other embodiments the substance determining apparatus can be adapted such that it comprises only one of these means, i.e. means for generating FTIR sensing signals or means for generating DFM sensing signals, as long as the generated sensing signals allow the binding event determination unit to determine binding events indicating a binding of a particle on the binding surface, in particular, lifetimes of the binding events, from the generated sensing signal.

Although in a described embodiment the analyzing device is a handheld device, in other embodiments the analyzing device can also be a standalone system which is to be arranged on, for example, a table.

The substance determining apparatus can be adapted to determine the amount and/or concentration of particles of a certain substance, if several substances are present within the fluid, wherein particles of these difference substances can bind to the binding surface, and wherein the bound particles of different substances are distinguished by using the determined different kinds of binding.

In the above described embodiment, the fluid was preferentially blood. In other embodiments, the fluid can be any other fluid, in particular, another body fluid, like saliva or urine. The preferred application for the binding device and for the analyzing device is in the field of point-of-care diagnostics, in particular, based on a finger prick blood sample, like a cardiac marker detection application. But, as mentioned above, the binding device can also be adapted for being used with other fluids like saliva for Drugs Of Abuse.

In the above described embodiments, the analyzing device apparatus uses evanescent field techniques for determining the amount of magnetic beads on the surface. In other embodiments, other techniques can be used for determining these beads. For example, magnetic methods, sonic detection, electrical detection and combinations therefore can be used. Furthermore, the analyzing device can comprise any sensor based on the detection of the magnetic properties of the beads on or near to a sensor surface. The analyzing device can be adapted for detecting molecular targets, which often determine the concentration and/or presence of larger moieties, for example, cells, viruses, fractions of cells or fractions of viruses, tissue extract et cetera. The magnetic beads can be detected directly by the sensing method. As well, the particles can be further processed prior to detection. An example of further processing is that materials are added or that the chemical, biochemical or physical properties of the magnetic labels are modified to facilitate detection. The analyzing device can be adapted for working together with several biochemical assay types, for example, binding/unbinding assay, sandwich assay, competition assay, displacement assay, enzymatic assay et cetera. The binding device and the analyzing device can be adapted for sensor multiplexing, i.e. the parallel use of different sensors and sensor surfaces, label multiplexing, i.e. the parallel use of different types of labels, and chamber multiplexing, i.e. the parallel use of different reaction chambers. The binding device and the analyzing device can be used as rapid, robust and easy to use point-of-care biosensors for small sample volumes. The sensing cavity is preferentially a part of a disposable cartridge, which is to be used with the analyzing device, which contains one or more magnetic field generating means, i.e. the magnetic unit, and one or more detection means. The binding device and the analyzing device can preferentially be adapted for use in automated high-throughput testing.

The particles are preferably magnetic beads being preferentially nano-particles having at least one dimension ranging between 3 nm and 5000 nm, preferably between 10 nm and 3000 nm, more preferred between 50 nm and 1000 nm.

Although in the above described embodiments a certain binding device and a certain analyzing device have been described, in other embodiments the binding device and the analyzing device can have another structure. For example, the binding device can just comprise a binding surface. Or another kind of filter can be used or another channel structure can be used for transferring filtered fluid from a filter location to a sensing location.

Although in the above described embodiments the substance determining apparatus is comprised of a binding device and an analyzing device, in another embodiment the substance determining apparatus can be an integrated apparatus comprising at least the particles, the binding surface, the sensing unit, the binding event determination unit and the substance determination unit.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of binding events, in particular, their lifetimes, or the determination of the substance, in particular, of the amount and/or concentration of the substance, within the fluid performed by one or several units or devices can be performed by any other number of units or devices. For example, steps 107 and 108 can be performed by a single unit or by any other number of different units. The determinations and/or the control of the substance determining apparatus, in particular, of the analyzing device, in accordance with the substance determining method, in particular, in accordance with the analyzing method, can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a substance determining apparatus for determining a substance within a fluid. Particles attach the substance and bind to a binding surface, wherein a sensing signal is generated depending on the bound particles. Binding events indicating a binding of a particle on the binding surface are determined from the generated sensing signal, and the substance within the fluid is determined based on the determined binding events. During a procedure of determining a substance within a fluid, particles may bind to the binding surface and may leave the binding surface. Therefore, during this procedure a number of binding events can be determined being much larger than the number of bound particles. The determination of the substance within the fluid can therefore be based on a very large amount of data, thereby increasing the accuracy of determining the substance within the fluid.

The invention claimed is:

1. A substance determining apparatus for determining a substance within a fluid, the substance determining apparatus comprising:
    particles configured to attach to the substance within the fluid,
    a binding surface configured to bind the particles which have been attached to the substance,
    a sensing unit configured to sense the bound particles bound on the binding surface, the sensing unit including:
        a light source configured to generate radiation which forms an evanescent field on the binding surface,
        a first objective lens configured to collect scattered light from the evanescent field, the scattered light scattered by the bound particles on the binding surface,
        a Dark Field Microscopy (DFM) detector configured to receive the collected scattered light and generate a DFM sensing signal based on Dark Field Microscopy (DFM),
        wherein the DFM detector is configured to generate images indicative of starting moments and ending moments of binding events,
        a second objective lens configured to collect reflected light from the evanescent field, the collected reflected light comprising light being internally reflected at the binding surface, and
        a Frustrated Total Internal Reflection (FTIR) detector configured to receive the collected reflected light beam and generate a FTR sensing signal based on Frustrated Total Internal Reflection,
    a binding event determination unit configured to receive the images from the Dark Field Microscopy (DFM) detector and the FTIR sensing signal and to determine lifetimes of binding events by determining the starting moments and the ending moments of at least a portion of individual binding events from the generated images and the second sensing, signal,
    a substance determination unit configured to determine the substance within the fluid based on the determined binding events and the determined lifetimes.

2. The substance determining apparatus according to claim 1, wherein the DFM detector is configured to generate images of the binding surface at different times, wherein the images show positions on the binding surface at which the particles are bound at a time corresponding to the images, wherein the binding event determination unit is further configured to receive the images from the DFM detector and determine the starting moments and the ending moments by comparing temporally consecutive images.

3. The substance determining apparatus according to claim 2, wherein the binding event determination unit is further configured to generate a histogram of lifetimes of the binding events by correlating the images of the binding surface at different times with the determined lifetimes of respective binding events;
    wherein the substance determination unit is further configured to determine the substance within the fluid based on the histogram.

4. The substance determining apparatus according to claim 1, wherein the particles and the binding surface comprise a binding device and the sensing unit, the binding event determining unit and the substance determining unit comprise an analyzing device.

5. The substance determining apparatus according to claim 1, wherein the Dark Field Microscopy (DFM) and FTIR detectors are configured to communicate with the binding event determination unit and the binding event determination unit is further configured to determine binding events indicating the binding of a particle on the binding surface from the generated first and second sensing signals.

6. The substance determining apparatus according to claim 4, wherein the sensing unit comprises a force applying unit configured to apply a force to the particles for putting bindings between the particles and the binding surface under stress, and to pull the particles away from the binding surface, the force applying unit including:
    a first magnet in a planar arrangement on a first side of the binding device, and
    a second magnet arranged on an opposite second side of the binding device.

7. A method for determining a substance within a fluid, comprising:
    attaching particles to the substance within the fluid,
    binding the particles which have attached to the substance to the binding surface,
    sensing the particles on the binding surface by the sensing unit, and generating the sensing signal which is dependent on the bound particles, the sensing including:
        generating radiation which forms an evanescent field on the binding surface,
        with a first objective lens, collecting a scattered light beam from the evanescent field, the scattered light beam scattered by the bound particles on the binding surface, and
        with a Dark Field Microscopy (DFM) detector, receiving the collected scattered light, and generating a DFM sensing signal based on Dark Field Microscopy,
        with the DFM detector, generating images indicative of starting moments and ending moments of binding events of the particles on the binding surface,
        with a second objective lens collecting reflected light,
        with a Frustrated Total Internal Reflection (FTIR) detector, receiving the collected reflected light and generating a FTIR sensing signal based on Frustrated Total Internal Reflection,
        determining lifetimes of the binding events from the indicated starting moments and ending moments of the binding units in the images from the DFM detector and the second sensing signals, and
        with a substance determination unit, determining the substance within the fluid based on the determined binding events including the determined lifetimes.

8. The method for determining a substance within a fluid according to claim 7, wherein the images of the binding surface are generated at different times and the determining the lifetimes further includes generating a histogram of the lifetimes of the binding events by correlating the images of the binding surface at different times with determined lifetimes of respective binding events.

9. The method for determining a substance within a fluid according to claim 8, wherein the determining binding events further includes determining a part of the histogram depending on a temporal behavior of the histogram being indicative of a certain kind of binding, and the determining the substance within the fluid further includes determining the substance based on the determined part of the histogram being indicative of the certain kind of binding.

10. The method for determining a substance within a fluid according to claim 8, wherein the determining binding events further includes:
    providing a fitting curve comprising a combination of a) a first product of a first number of binding events with a predefined lifetime and a first exponential decay fitting curve having a first time constant and b) a second product of a second number of binding events with the predefined lifetime and a second exponential decay fitting curve having a second time constant,
    fining the fitting curve to the histogram, wherein the first number of binding events, the first time constant, the second number of binding events and the second time constant are fitting parameters, determine the part of the histogram being indicative of the certain kind of binding depending on at least one of the first exponential decay fitting curve with the fitted first number of binding events and first time constant and the second exponential decay fitting curve with the fitted second number of binding events and second time constant.

11. A substance determining apparatus for determining a substance within a fluid, the substance determining apparatus comprising:
    particles configured to attach to the substance within the fluid,
    a binding surface configured to bind the particles which have been attached to the substance,
    a light source configured to generate radiation which forms an evanescent field on the binding surface,
    a first objective lens configured to collect a scattered light beam from the evanescent field, wherein the scattered light beam is scattered by the bound particles on the binding surface,
    an imaging lens configured to focus the scattered light into images indicative of starting moments and ending moments of binding events of the particles on the binding surface,
    a Dark Field Microscopy (DFM) detector configured to receive the scattered light images and DFM signals indicative of the starting moments and the ending moments of the binding events,
    a second objective lens configured to collect reflected light from the evanescent field;
    a Frustrated Total Internal Reflectance (FTIR) detector configured to receive the collected reflected light from the second objective lens and generate a FTIR signal therefrom, and
    a computer programmed with a computer program configured to:
        receive the DFM signals and the FTIR signal,
        determine lifetimes of the binding events from the starting moments and the ending moments of at least a portion of the binding events from the DFM signals and the FTIR signal,
        determine the substance in the fluid based on the determined lifetimes and the determined binding events.

12. A method for determining a substance within a fluid, comprising:
    attaching particles to the substance within the fluid,
    binding the particles which have attached to the substance to the binding surface,
    sensing the particles on the binding surface by the sensing unit, and generating the sensing signal which is dependent on the bound particles, the sensing including:
        generating radiation which forms an evanescent field on the binding surface,
        with a first objective lens, collecting a scattered light beam from the evanescent field, the scattered light beam scattered by the bound particles on the binding surface, and
        with a Dark Field Microscopy (DFM) detector, receiving the collected scattered light, and generating a DFM signal,
        with the DFM detector generating images indicative of starting moments and ending moments of binding events of the particles on the binding surface using DFM,
        with a second objective lens, focusing reflected light on a Frustrated Total Internal Reflectance (FTIR) detector,
        with the FTIR detector, generating a FTIR signal, determining lifetimes of the binding events from the indicated starting moments and ending moments of the binding units in the images from the DFM detector and the FTIR signal, and with a substance determination unit, determining the substance within the fluid based on the determined binding events including the determined lifetimes of the binding events.

\* \* \* \* \*